United States Patent
Park et al.

(10) Patent No.: US 10,376,239 B2
(45) Date of Patent: Aug. 13, 2019

(54) ULTRASONIC IMAGING APPARATUS AND METHOD OF PROCESSING ULTRASOUND IMAGE

(71) Applicant: SAMSUNG MEDISON CO., LTD., Hongcheon-gun (KR)

(72) Inventors: Tae-jin Park, Hongcheon-gun (KR); Dae-woong Kang, Hongcheon-gun (KR); Yea-chan Choi, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 727 days.

(21) Appl. No.: 14/948,538

(22) Filed: Nov. 23, 2015

(65) Prior Publication Data

US 2016/0183923 A1 Jun. 30, 2016

(30) Foreign Application Priority Data

Dec. 29, 2014 (KR) .......................... 10-2014-0192554

(51) Int. Cl.
| | |
|---|---|
| *A61B 8/14* | (2006.01) |
| *A61B 8/00* | (2006.01) |
| *A61B 8/08* | (2006.01) |
| *G16H 40/63* | (2018.01) |
| *G06F 19/00* | (2018.01) |

(52) U.S. Cl.
CPC .............. *A61B 8/463* (2013.01); *A61B 8/14* (2013.01); *A61B 8/465* (2013.01); *A61B 8/5207* (2013.01); *G06F 19/00* (2013.01); *G16H 40/63* (2018.01)

(58) Field of Classification Search
CPC ........... A61B 8/14; A61B 8/463; A61B 8/465; A61B 8/5207; G06F 19/00; G16H 40/63
See application file for complete search history.

(56) References Cited

U.S. PATENT DOCUMENTS

| | | | |
|---|---|---|---|
| 6,273,857 B1 | 8/2001 | Aden | |
| 7,044,912 B2 | 5/2006 | Babu et al. | |
| 7,857,764 B2 | 12/2010 | Mori | |
| 8,046,707 B2 | 10/2011 | Akaki | |
| 2007/0038086 A1* | 2/2007 | Ohtsuka | A61B 8/06 600/437 |
| 2011/0137169 A1 | 6/2011 | Akaki et al. | |
| 2013/0145269 A1 | 6/2013 | Latulipe et al. | |
| 2014/0059486 A1 | 2/2014 | Sasaki et al. | |
| 2014/0189560 A1 | 7/2014 | Caspi | |

FOREIGN PATENT DOCUMENTS

| | | |
|---|---|---|
| JP | 2005-13324 A | 1/2005 |
| JP | 2014-124235 A | 7/2014 |

OTHER PUBLICATIONS

Communication dated Jun. 28, 2016, issued by the European Patent Office in counterpart European Patent Application No. 15202734.8.

* cited by examiner

*Primary Examiner* — Mark D Remaly
(74) *Attorney, Agent, or Firm* — Sughrue Mion, PLLC

(57) ABSTRACT

Provided are an ultrasound imaging apparatus and a method of processing an ultrasound image. The ultrasound imaging apparatus includes a display configured to display a moving image consisting of a plurality of ultrasound images that are played back according to a time order together with at least one icon, corresponding to at least one piece of change information for changing a display of at least one of the plurality of ultrasound images, in association with the time order.

11 Claims, 17 Drawing Sheets

ULTRASONIC IMAGING APPARATUS AND METHOD OF PROCESSING ULTRASOUND IMAGE

RELATED APPLICATION

This application claims the benefit of Korean Patent Application No. 10-2014-0192554, filed on Dec. 29, 2014, in the Korean Intellectual Property Office, the disclosure of which is incorporated herein in its entirety by reference.

BACKGROUND

1. Field

One or more exemplary embodiments relate to an ultrasound imaging apparatus for displaying a screen including an ultrasound image and a method of processing an ultrasound image.

2. Description of the Related Art

Due to its non-invasive and non-destructive nature, an ultrasound system has become widely used in many medical fields that require information about the inside of an object. The ultrasound system also plays a critical role in medical diagnosis since it can provide high-resolution images of internal tissues of an object to a medical practitioner without the need for performing a surgical procedure to directly incise the object for observation.

A user may view a moving image consisting of a plurality of ultrasound images. Furthermore, the user may change a display of at least one of the plurality of ultrasound images, e.g., by enlarging or reducing a specific region in the at least one ultrasound image.

SUMMARY

One or more exemplary embodiments include an ultrasound imaging apparatus and method that are capable of displaying a moving image consisting of a plurality of ultrasound images that are played back according to a time order together with an icon, corresponding to change information for changing a display of an ultrasound image, in association with the time order.

Additional aspects will be set forth in part in the description which follows and, in part, will be apparent from the description, or may be learned by practice of the presented exemplary embodiments.

According to one or more exemplary embodiments, an ultrasound imaging apparatus includes a display configured to display a moving image consisting of a plurality of ultrasound images that are played back according to a time order together with at least one icon, corresponding to at least one piece of change information for changing a display of at least one of the plurality of ultrasound images, in association with the time order.

The ultrasound imaging apparatus may further include a user interface configured to receive a first input for selecting the at least one icon.

The ultrasound imaging apparatus may further include a controller configured to change, if the first input is received, the at least one ultrasound image according to the at least one piece of change information and control the changed ultrasound image to be displayed via the display.

The display may display at least one thumbnail image corresponding to the at least one ultrasound image according to the time order, and the user interface may receive a second input for selecting the at least one thumbnail image. The apparatus may further include a controller configured to control, if the second input is received, the at least one ultrasound image corresponding to the at least one thumbnail image to be displayed via the display.

The at least one piece of change information may include at least one selected from the group consisting of information for inserting a predetermined letter or image into the at least one ultrasound image, information for changing an imaging mode for the at least one ultrasound image, and information for enlarging or reducing the at least one ultrasound image.

The display may display a progress indicator representing the time order and further displays the at least one icon.

The display may display the at least one icon at a position close to a time point within the progress indicator when the at least one ultrasound image is displayed.

The progress indicator may be displayed based on a time when the plurality of ultrasound images are displayed or based on the number of ultrasound images displayed among the plurality of ultrasound images.

The display may display the at least one piece of change information that is classified according to a predetermined criterion or arranged according to an order in which the at least one piece of change information is generated.

The ultrasound imaging apparatus may further include: an image acquisition unit configured to acquire the plurality of ultrasound images; a controller configured to generate the at least one piece of change information based on a user input; and a memory configured to store the at least one piece of change information as metadata.

The image acquisition unit may transmit an ultrasound signal to an object over a predetermined period and generate the plurality of ultrasound images based on an echo signal reflected from the object.

According to one or more exemplary embodiments, a method of processing an ultrasound image includes: displaying a moving image consisting of a plurality of ultrasound images that are played back according to a time order together with at least one icon, corresponding to at least one piece of change information for changing a display of at least one of the plurality of ultrasound images, in association with the time order; and receiving a first input for selecting the at least one icon.

According to one or more exemplary embodiments, a non-transitory computer-readable recording medium has recorded thereon a program for executing the above method on a computer.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
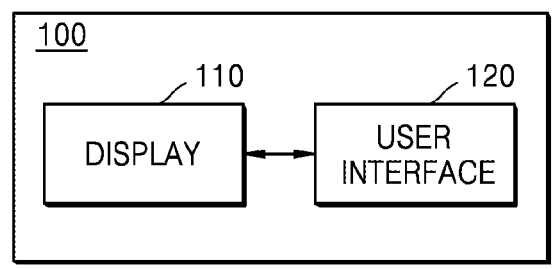
FIG. 1 is a block diagram of an ultrasound imaging apparatus according to an exemplary embodiment.

Reference will now be made in detail to exemplary embodiments, examples of which are illustrated in the accompanying drawings, wherein like reference numerals refer to like elements throughout. The exemplary embodiments set forth herein should be considered in a descriptive sense only and not for purposes of limitation. Other features or embodiments that will be readily apparent to those of ordinary skill in the art from the following descriptions and embodiments will be construed as being included in the present inventive concept. Expressions such as "at least one of," when preceding a list of elements, modify the entire list of elements and do not modify the individual elements of the list.

The terms used in this specification are those general terms currently widely used in the art in consideration of functions regarding the present invention, but the terms may vary according to the intention of those of ordinary skill in the art, precedents, or new technology in the art.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, it will be understood that when an element is referred to as being "connected" or "coupled" to another element, it can be directly connected to or electrically coupled to the other element with one or more intervening elements interposed therebetween.

Throughout the specification, an "object" may be a living or non-living thing of which image is to be generated. The object may also be a part of a human body. In this case, the object may include an internal organ such as the liver, the heart, the womb, the brain, a breast, or the abdomen, a fetus, etc. The object may also include a cross-section of the human body.

A "medical image" may be an ultrasound image or all other images generated using medical imaging techniques such as magnetic resonance imaging (MRI), computed tomography (CT), and positron emission tomography (PET). The images are obtained by reconstructing a cross-section or volume data of a tissue of a human body from a signal projected onto the tissue and are used for diagnosis and treatment of diseases.

Throughout the specification, a "user" may be, but is not limited to, a medical expert such as a medical doctor, a nurse, a medical laboratory technologist, a sonographer, or a medical imaging expert.

Exemplary embodiments will now be described in detail with reference to the accompanying drawings.

FIG. 1 is a block diagram of an ultrasound imaging apparatus 100 according to an exemplary embodiment. The ultrasound imaging apparatus 100 according to the present exemplary embodiment may be a cart type apparatus or a portable type apparatus. The ultrasound imaging apparatus 100 refers to an apparatus for providing a user with a medical image of an object via a screen. Examples of a portable type medical image display apparatus may include, but are not limited to, a picture archiving and communication system (PACS) viewer, a smartphone, a laptop computer, a personal digital assistant (PDA), and a tablet PC.

Referring to FIG. 1, the ultrasound imaging apparatus 100 may include a display 110 and a user interface 120. Although FIG. 1 shows that the ultrasound imaging apparatus 100 includes only the components related to the present exemplary embodiment, it will be understood by those of ordinary skill in the art that the ultrasound imaging apparatus 100 may further include other components than those shown in FIG. 1.

According to an exemplary embodiment, the display 110 consecutively displays a plurality of ultrasound images according to a time order. The display 110 also displays on a screen a moving image consisting of the plurality of ultrasound images that are reproduced time-sequentially. Furthermore, the display 110 displays, together with the moving image, at least one icon, corresponding to at least one piece of change information for changing a display of at least one of the plurality of ultrasound images displayed on the screen, in association with the time order. According to an exemplary embodiment, the display 110 may display different icons corresponding to different kinds of change information in order to identify the different kinds of change information.

According to an exemplary embodiment, the display 110 may display a progress indicator representing the time order in which a moving image is reproduced together with an icon corresponding to change information. In detail, the progress indicator may represent a status or progress of reproduction of a moving image over time. For example, the progress indicator may be a progress bar. Furthermore, the progress indicator may be displayed based on the time when ultrasound images of a moving image are reproduced or the number of ultrasound images displayed as the moving image is reproduced.

Change information refers to information for changing a display of an ultrasound image. For example, the change information may be information for inserting a letter or image into an ultrasound image, information for changing an imaging mode for an ultrasound image, or information for displaying an enlarged or reduced version of an ultrasound image. Examples of change information will be described in more detail below with reference to FIG. 10.

Furthermore, according to an exemplary embodiment, the display 110 may display a thumbnail image, corresponding to a predetermined image among a plurality of ultrasound images, in association with the time order in which a moving image is reproduced.

According to an exemplary embodiment, if a plurality of pieces of change information are generated for a moving image, the display 110 may display the plurality of pieces of change information that are classified according to a predetermined criterion. A more detailed exemplary embodiment thereof will be described below with reference to FIG. 11.

The display 130 of FIG. 1 may display information processed by the medical image display apparatus 100. For example, the display 130 may display an ultrasound image, or a user interface (UI) or graphic user interface (GUI) related to setting of functions of the ultrasound imaging apparatus 100.

The display 110 may include at least one selected from a liquid crystal display (LCD), a thin-film transistor-LCD (TFT-LCD), an organic light-emitting diode (OLED), a flexible display, a three-dimensional (3D) display, and an electrophoretic display. According to exemplary embodiments, the ultrasound imaging apparatus 100 may include two or more displays 110.

The user interface 120 receives a first input for selecting at least one icon displayed via the display 110. According to an exemplary embodiment, the user interface 120 may receive an input for selecting at least one of a plurality of ultrasound images displayed on a screen. The user interface 120 may also receive a user input for changing a display of at least one ultrasound image. Furthermore, the user interface 120 may receive a user input for requesting a screen shot of at least one ultrasound image displayed via the display 110.

According to an exemplary embodiment, the user interface 120 may receive a user input for stopping a consecutive display of a plurality of ultrasound images based on a first one of the ultrasound images. For example, if a first one of a plurality of ultrasound images that are to be consecutively displayed is displayed, the user interface 120 may receive a freeze signal for temporarily stopping a consecutive display of the ultrasound images from a user, and accordingly, the display 110 may display only the first ultrasound image. Then, the user interface 120 may receive a signal for terminating the freeze signal from the user, and accordingly, the display 110 may consecutively display subsequent ultrasound images.

The user interface 120 may include a device for receiving a predetermined input from the outside. Examples of the user interface 120 may include a microphone, a keyboard, a mouse, a joystick, a touch pad, a touch pen, a voice recognition sensor, a gesture recognition sensor, etc.

According to an exemplary embodiment, the user interface 120 may receive a user input for selecting an icon displayed on a screen. If the user interface 120 receives an input for selecting an icon, the display 110 may display on the screen an ultrasound image changed according to change information corresponding to the selected icon. Furthermore, according to an exemplary embodiment, the user interface 120 may receive a user input for selecting a thumbnail image for an ultrasound image. For example, if the user interface 120 receives an input for selecting a thumbnail image, the display 110 may display an ultrasound image corresponding to the selected thumbnail image on the screen.

Figure 2:
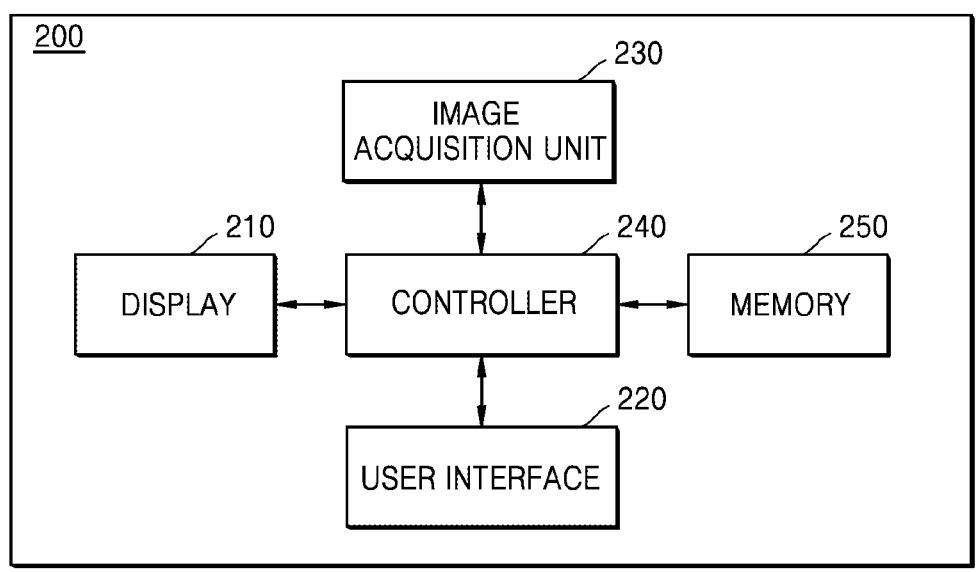
FIG. 2 is a block diagram of an ultrasound imaging apparatus according to another exemplary embodiment.

FIG. 2 is a block diagram of an ultrasound imaging apparatus 200 according to another exemplary embodiment.

Referring to FIG. 2, the ultrasound imaging apparatus 200 according to the present exemplary embodiment may include a display 210, a user interface 220, an image acquisition unit 230, a controller 240, and a memory 250. Although FIG. 2 shows that the ultrasound imaging apparatus 200 includes only the components related to the present exemplary embodiment, it will be understood by those of ordinary skill in the art that the ultrasound imaging apparatus 200 may further include other components than those shown in FIG. 2.

The descriptions of the display 110 and the user interface 120 of FIG. 1 are included in the descriptions of the display 210 and the user interface 220 shown in FIG. 2, and thus, are not repeated.

According to an exemplary embodiment, the image acquisition unit 230 may acquire a plurality of ultrasound images that are to be sequentially displayed. The image acquisition unit 230 may also acquire a moving image consisting of a plurality of ultrasound images that are reproduced time-sequentially. According to an exemplary embodiment, the image acquisition unit 410 may include an ultrasound probe for transmitting or receiving ultrasound waves directly to or from an object. The ultrasound probe may transmit ultrasound signals to the object in response to a driving signal applied thereto and receive echo signals reflected from the object.

The ultrasound data acquisition unit 410 acquires ultrasound data related to an object. In detail, the ultrasound data acquisition unit 410 may transmit ultrasound signals to the object and acquire ultrasound data based on echo signals reflected from the object.

The ultrasound probe includes a plurality of transducers, and the plurality of transducers oscillate in response to electric signals and generate acoustic energy, i.e., ultrasound waves. Furthermore, the ultrasound probe may be connected to a main body of the ultrasound imaging apparatus 200 by wire or wirelessly. According to exemplary embodiments, the ultrasound imaging apparatus 200 may include a plurality of ultrasound probes. An ultrasound probe according to an exemplary embodiment may include at least one selected from a 1-dimensional (1D) probe, a 1.5-dimensional (1.5D) probe, a two-dimensional (2D) (matrix) probe, and a 3D probe.

Thus, the image acquisition unit 230 may transmit an ultrasound signal to an object over a predetermined period via an ultrasound probe and generate a plurality of ultrasound images of the object based on an echo signal reflected from the object. Thus, the image acquisition unit 230 may acquire a moving image from the generated ultrasound images.

Thus, the display 210 may display the generated ultrasound images in real-time, and the memory 250 may store a moving image in which the ultrasound images are sequentially displayed.

According to an exemplary embodiment, the image acquisition unit 230 may also acquire a moving image consisting of a plurality of ultrasound images reproduced from the outside via a communication module (not shown). Furthermore, the image acquisition unit 230 may acquire a plurality of prestored ultrasound images from the memory 250.

According to an exemplary embodiment, based on a user input received via the user interface 220, the controller 240 may generate at least one piece of change information for changing a display of at least one of a plurality of ultrasound images. The controller 240 may also generate an icon identifying change information and control the generated icon to be displayed via the display 210. Furthermore, if the user interface 220 receives an input for selecting an icon from the user, the controller 240 may change an ultrasound image according to change information corresponding to the icon and control the changed ultrasound image to be displayed via the display 210.

According to an exemplary embodiment, the controller 240 may also take a screen shot of at least one of a plurality of ultrasound images based on a user input received via the user interface 220, thereby generating a thumbnail image for the at least one ultrasound image. A screen shot refers to an image obtained by capturing an image currently being displayed on the screen via the display 210 and preserving it as a file. Thus, the controller 240 may control the thumbnail image to be displayed via the display 210 together with a progress indicator. Furthermore, if the user interface 220 receives an input for selecting a thumbnail image from the user, the controller 240 may control an ultrasound image corresponding to the thumbnail image to be displayed via the display 210.

Furthermore, the user interface 220 may receive a user input for stopping reproduction of a moving image. In this case, the controller 240 may stop the reproduction of the moving image at the moment when a first ultrasound image in the moving image is displayed. Subsequently, the controller 240 may generate change information for changing a display of the first ultrasound image based on the user input.

Based on a user input received via the user interface 220, the controller 240 may also classify at least one piece of change information according to a predetermined criterion. For example, the user interface 220 may receive input information for classifying pieces of change information of a moving image into a plurality of categories from the user, and the controller 240 may classify the change information of the moving image according to the input information. The controller 240 may also control icons corresponding to the change information to be displayed via the display 210, as described in more detail below with reference to FIG. 11.

According to an exemplary embodiment, the memory 250 may store at least one piece of change information as metadata. Metadata refers to data providing information directly or indirectly associated with data such as moving images, sounds, and documents. Thus, the memory 250 may store metadata containing change information of each moving image acquired by the image acquisition unit 230.

Furthermore, the controller 240 may classify at least one piece of change information based on the metadata stored in the memory 250 and control icons corresponding to the at least one piece of classified change information to be displayed via the display 210.

Thus, according to the present disclosure, the user may simultaneously check a moving image displayed by the ultrasound imaging apparatus 100 (200) as well as icons representing pieces of change information related to the moving image, and thus identify the pieces of change information related to the moving image in advance before viewing the entire moving image. Furthermore, the ultrasound imaging apparatus 100 (200) may selectively display change information desired by the user among the pieces of change information related to the moving image.

Furthermore, the memory 250 may store a moving image in which a plurality of ultrasound images are reproduced time-sequentially. In addition, if at least one ultrasound image is changed according to at least one piece of change information, the memory 250 may store the changed ultrasound image.

Figure 3:
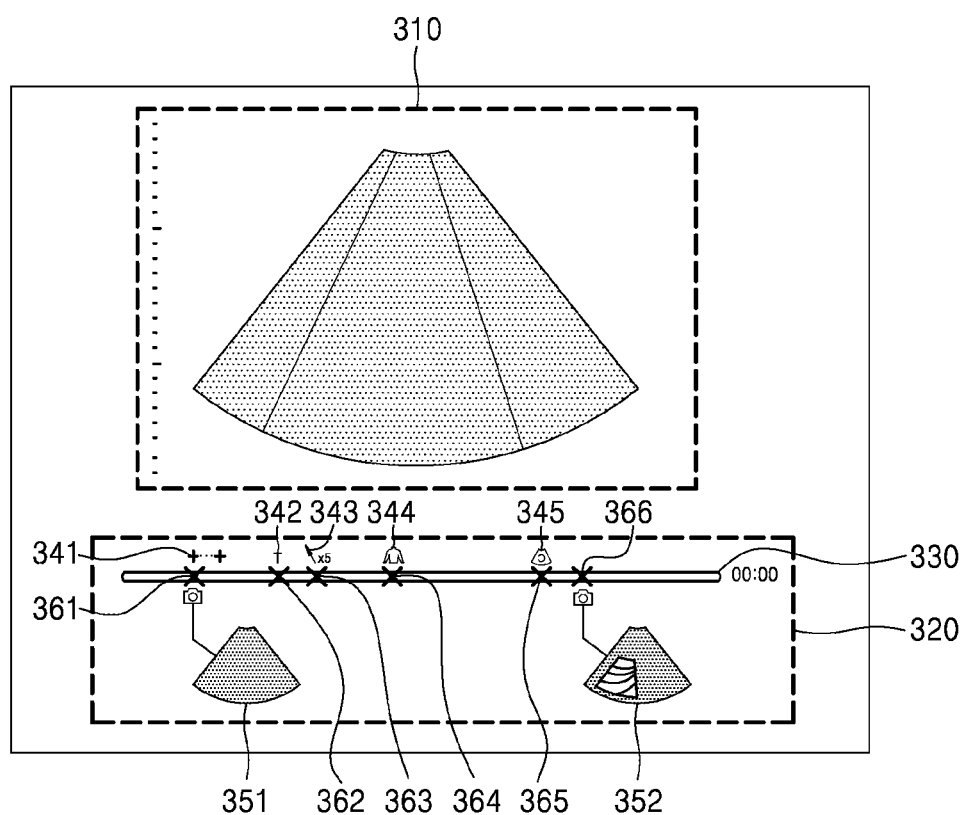
FIG. 3 is a diagram for explaining an example where an ultrasound imaging apparatus displays an ultrasound image.

FIG. 3 is a diagram for explaining an example where the ultrasound imaging apparatus 100 (200) displays an ultrasound image. For convenience of explanation, the ultrasound imaging apparatus 100 (200) is hereinafter referred to as the apparatus 100 (200).

The apparatus 100 (200) may display first and second regions 310 and 320 on the screen via the display 110 (210). The first region 310 depicts a plurality of ultrasound images that are sequentially displayed as a moving image is reproduced. The second region 320 displays a progress indicator 330 indicating the time order in which the plurality of ultrasound images in the moving image is reproduced, icons 341 through 345 for identifying pieces of change information corresponding thereto, and thumbnail images 351 and 352. The moving image displayed in the first region 310 may be a moving image prestored in the apparatus 100 (200) or showing a plurality of ultrasound images generated by the apparatus 100 (200) using an ultrasound signal. As shown in FIG. 3, the thumbnail images 351 and 352 may be displayed by adding camera-shaped icons thereto. Although FIG. 3 shows that the progress indicator 330 is displayed in unit of time, exemplary embodiments are not limited thereto, and the progress indicator 330 may be displayed in unit of the number of ultrasound image frames in the moving image. For example, the progress indicator 330 may show the lapse of time and move from left to right as time passes.

Based on a user input, the apparatus 100 (200) may display in the second region 320 the icons 341 through 345 corresponding to the pieces of change information for changing a display of ultrasound images selected by the user. According to an exemplary embodiment, the apparatus 100 (200) may display the icons 341 through 345 representing the pieces of change information of ultrasound images displayed at time points 361 through 365 within the progress indicator 330, in association with the progress indicator 330.

In detail, the icon 341 represents change information for adding measurement information of a specific region in the ultrasound image displayed at the time point 361 to the ultrasound image, as described in more detail below with reference to FIG. 5.

The icon 342 represents change information for adding an annotation to the ultrasound image displayed at the time point 362 according to a user input, as described in more detail below with reference to FIG. 6.

The icon 343 represents change information for adding a pointer marker to the ultrasound image displayed at the time point 363 according to a user input. '×5' within the icon 363 indicates that five (5) pointer markers, to be added to specific points, have been set in the ultrasound image, as described in more detail below with reference to FIG. 7.

The icon 344 represents change information for attaching a body marker to the ultrasound image displayed at the time point 364 according to a user input. The body marker is an annotation indicated by a predetermined image and indicates which part of a body corresponds to a specific region in an ultrasound image, as described in more detail below with reference to FIG. 8.

The icon 345 represents change information for changing an imaging mode for the ultrasound image displayed at the time point 365, as described in more detail below with reference to FIG. 9.

Furthermore, the apparatus 100 (200) may take screen shots of the ultrasound images displayed at the time points 361 and 365 based on a user input, thereby displaying the thumbnail images 351 and 352 for the ultrasound images in association with the progress indicator 330. If the thumbnail images 351 and 352 are selected according to a user input, the apparatus 100 (200) may display the ultrasound images corresponding to the thumbnail images 351 and 352 in the first region 310.

Figure 4:
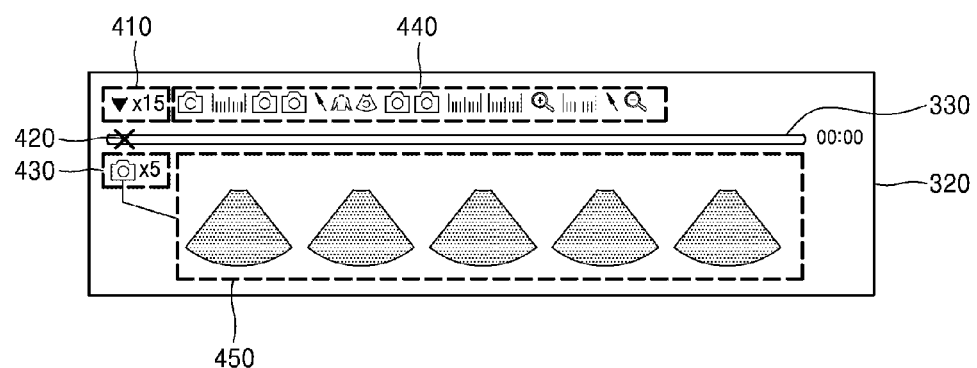
FIG. 4 illustrates a second region shown in FIG. 3 according to an exemplary embodiment.

FIG. 4 illustrates the second region 320 shown in FIG. 3 according to an exemplary embodiment.

Referring to FIG. 4, the apparatus 100 (200) may display icons 410, 430, and 440, the progress indicator 330, and five (5) thumbnail images 450 in the second region 320.

The apparatus 100 (200) may generate a plurality of pieces of change information for an ultrasound image displayed at a time point 420 within the progress indicator 330 based on a user input. Thus, the apparatus 100 (200) may display the icon 410 corresponding to the plurality of pieces of change information in association with the progress indicator 330. '×15' within the progress indicator 330 indicates that fifteen (15) pieces of change information are generated for the ultrasound image. If the apparatus 100 (200) receives an input for selecting the icon 410 from the user, a region including 15 icons corresponding to the 15 pieces of change information is created. The apparatus 100 (200) may then display the icon 440 representing the 15 pieces of change information.

Furthermore, the apparatus 100 (200) may take a plurality of screen shots of the ultrasound image displayed at the time point 420 within the progress indicator 330. Thus, the apparatus 100 (200) may display the icon 430 representing information indicating that the plurality of screen shots have been taken. If the apparatus 100 (200) receives an input for selecting the icon 430, the apparatus 100 (200) may display the 5 thumbnail images 450. Furthermore, according to an exemplary embodiment, each of the 5 thumbnail images 450 may be a thumbnail image for an ultrasound image changed according to at least one of the 15 pieces of change information.

Figure 5:
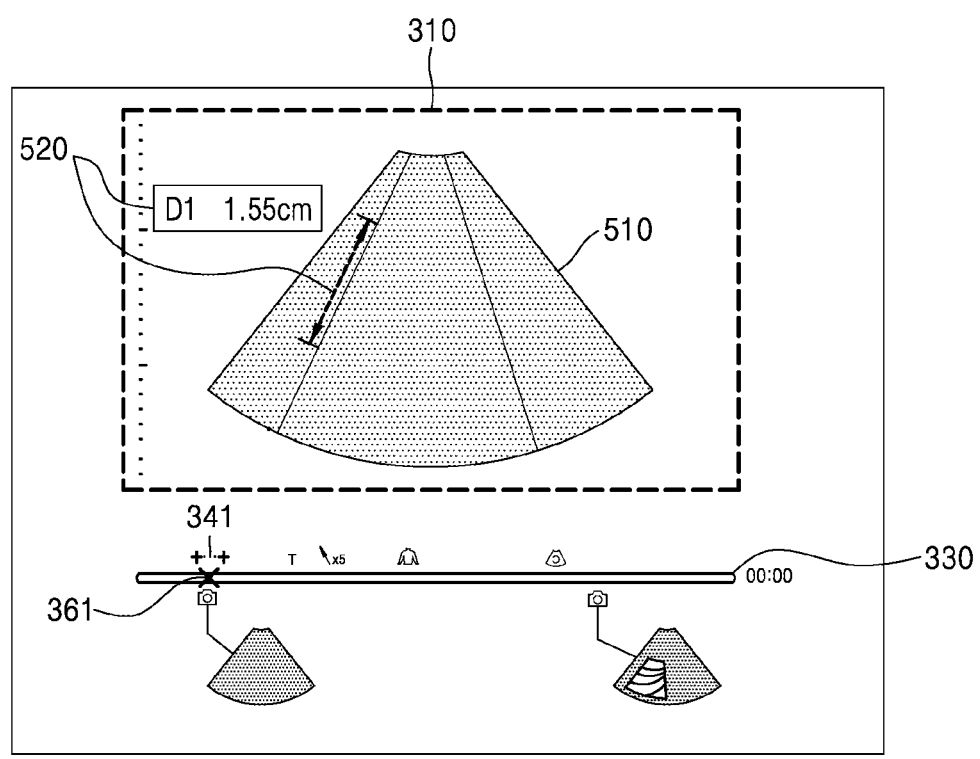
FIGS. 5 through 9 illustrate examples where an ultrasound imaging apparatus displays ultrasound images according to an exemplary embodiment.

FIG. 5 is a diagram for explaining an example where the ultrasound imaging apparatus 100 (200) displays an ultrasound image.

The apparatus 100 (200) may receive from the user an input for measuring a distance between two specific points in an ultrasound image 510 displayed at a time point 361 within a progress indicator 330. Then, the apparatus 100 (200) may generate change information for setting a display of measurement information 520 to be added to the ultrasound image 510. Thus, the apparatus 100 (200) may display an icon 341 representing the generated change information at a position near the time point 361. Although FIG. 5 shows that the measurement information 520 is obtained by measuring a linear distance between the two points, exemplary embodiments are not limited thereto, and the measurement information 520 may be obtained by measuring an angle between two straight lines or an area of a specific region. Furthermore, the user may generate the measurement information 520 using a function of a caliper within the apparatus 100 (200). In this case, a caliper may be a virtual measuring instrument that can be used to measure a length, a diameter, a width, etc., of a target (e.g., a specific fetal bone) within an object. A function of a caliper may be a function for obtaining measurement information by measuring the target.

The apparatus 100 (200) may also receive an input for selecting the icon 341 from the user and then display the ultrasound image 510 having the measurement information 520 added thereto in a first region 310 according to the change information.

Furthermore, although FIG. 5 shows the progress indicator 330 in the form of a progress bar, exemplary embodiments are not limited thereto, and the progress indicator 330 may have various other forms.

Figure 6:
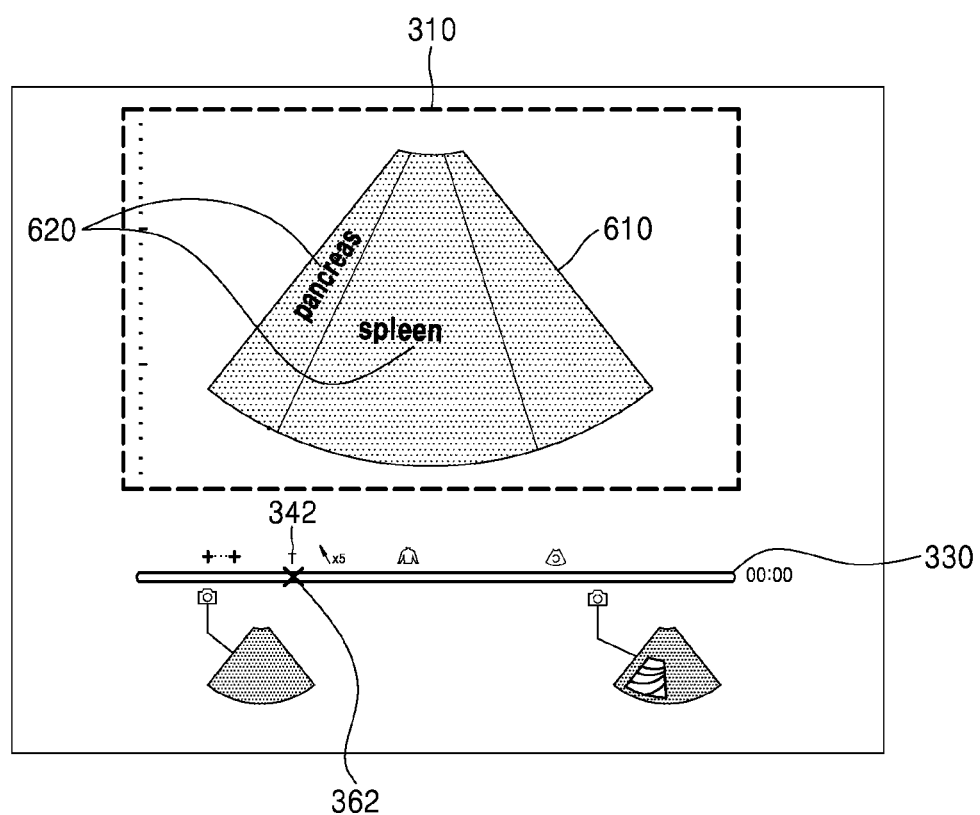

FIG. 6 is a diagram for explaining another example where the ultrasound imaging apparatus 100 (200) displays an ultrasound image.

The apparatus 100 (200) may receive from the user an input for inserting an annotation 620 into an ultrasound image 610 displayed at a time point 362 within a progress indicator 330. Then, the apparatus 100 (200) may generate change information for adding the annotation 620 to the ultrasound image 610. Thus, the apparatus 100 (200) may display an icon 342 representing the generated change information at a position near the time point 362. Although FIG. 6 shows that the annotation 620 is indicated by letters 'pancreas' and 'spleen', exemplary embodiments are not limited thereto, and the annotation 620 may be indicated by another letter or arbitrary image.

Furthermore, the apparatus 100 (200) may receive an input for selecting the icon 342 from the user and then display the ultrasound image 610 having the annotation 620 added thereto in a first region 310 according to the change information.

Figure 7:
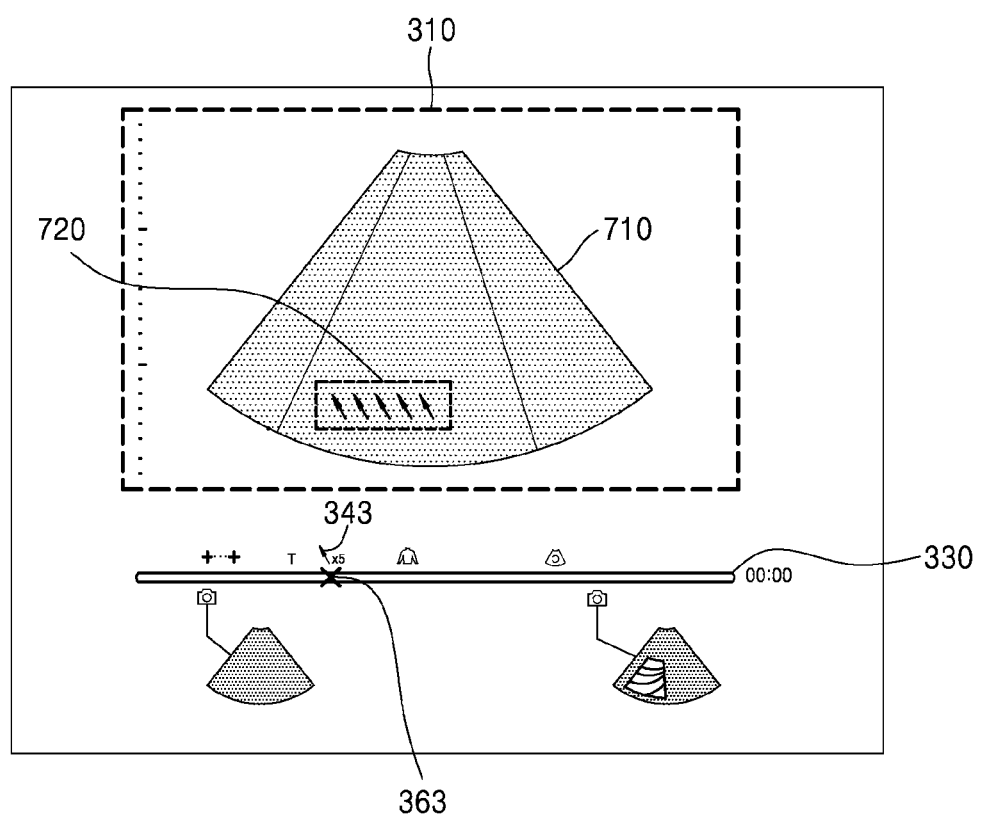

FIG. 7 is a diagram for explaining another example where the ultrasound imaging apparatus 100 (200) displays an ultrasound image.

The apparatus 100 (200) may receive from the user an input for inserting a pointer marker 720 into an ultrasound image 710 displayed at a time point 363 within a progress indicator 330. Then, the apparatus 100 (200) may generate change information for adding the pointer marker 720 to the ultrasound image 710. Thus, the apparatus 100 (200) may display an icon 343 representing the generated change information at a position near the time point 363. The pointer marker 720 is not limited to the form or total number shown in FIG. 7 and may have different shapes or include more or fewer pointer markers than five (5).

Furthermore, the apparatus 100 (200) may receive an input for selecting the icon 343 from the user and then display the ultrasound image 710 having the pointer marker 720 added thereto in a first region 310 according to the change information.

Figure 8:
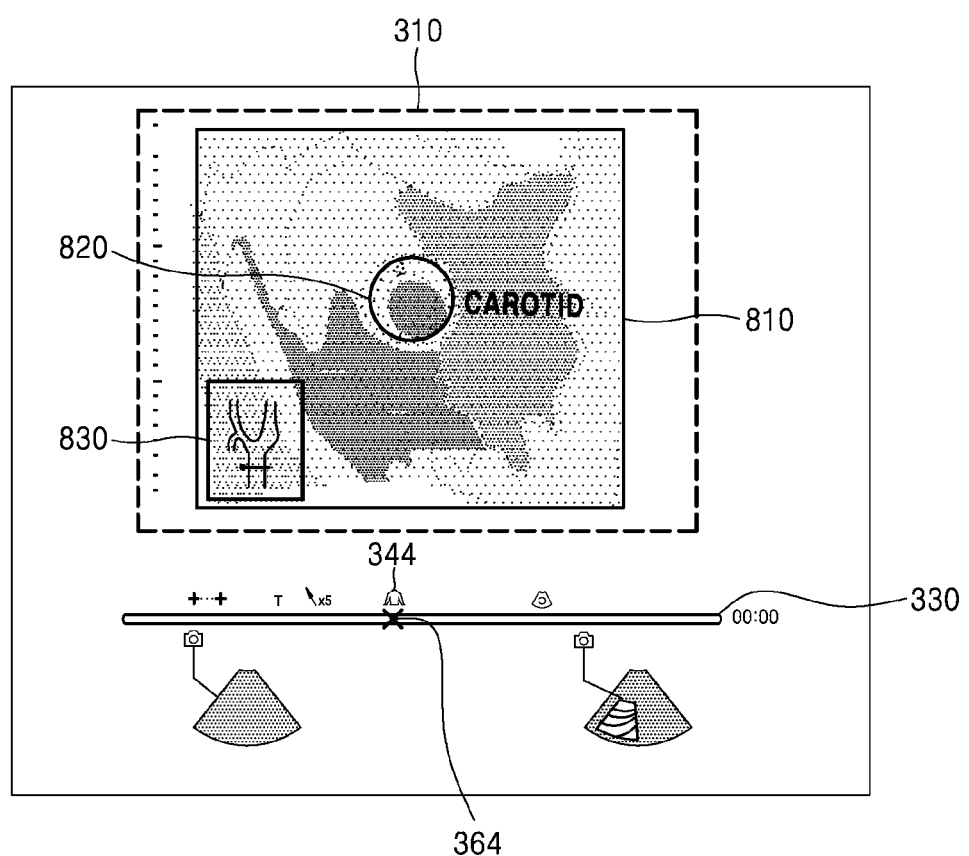

FIG. 8 is a diagram for explaining another example where the ultrasound imaging apparatus 100 (200) displays an ultrasound image.

The apparatus 100 (200) may receive from the user an input for inserting a body marker 830 indicating a specific region 820 in an ultrasound image 810 displayed at a time point 364 within a progress indicator 330. Then, the apparatus 100 (200) may generate change information for adding body marker information 820 and 830 to the ultrasound image 810. Thus, the apparatus 100 (200) may display an icon 344 representing the generated change information at a position near the time point 364. Although FIG. 8 shows the body marker 830 indicates which part of a body corresponds to the specific region 820 showing a carotid, exemplary embodiments are not limited thereto. Furthermore, the body marker 830 is not limited to a shape or location as shown in FIG. 8, and may have a different shape or be located at a different position on a screen.

Furthermore, the apparatus 100 (200) may receive an input for selecting the icon 344 from the user and then display the ultrasound image 810 having the body marker information 820 and 830 added thereto in a first region 310 according to the change information.

Figure 9:
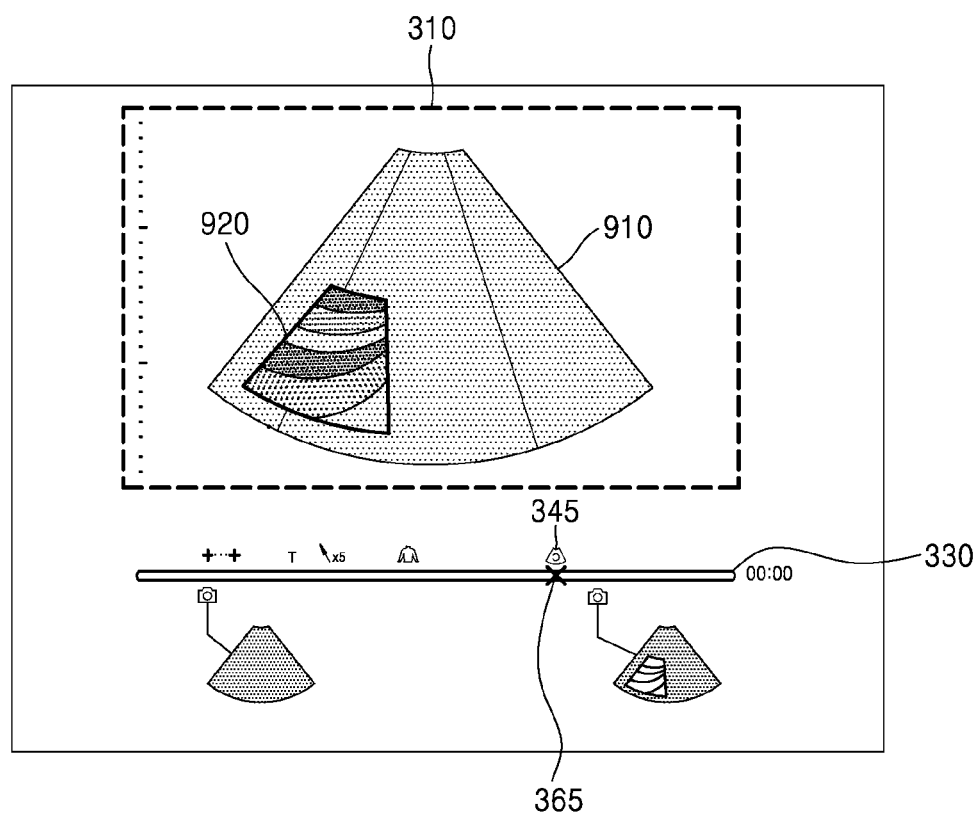

FIG. 9 is a diagram for explaining another example where the ultrasound imaging apparatus 100 (200) displays an ultrasound image.

The apparatus 100 (200) may receive from the user an input for changing an imaging mode with respect to a specific region 920 in an ultrasound image 910 displayed at a time point 365 within a progress indicator 330. Then, the apparatus 100 (200) may generate change information for adding the specific region 920, with respect to which the imaging mode has been changed, to the ultrasound image 910. Thus, the apparatus 100 (200) may display an icon 345 representing the generated change information at a position near the time point 365. Although FIG. 9 shows that an imaging mode for the specific region 920 is changed, the apparatus 100 (200) may generate change information for changing an imaging mode for the entire ultrasound image 910.

Furthermore, the apparatus 100 (200) may receive an input for selecting the icon 345 from the user and then display the ultrasound image 910 to which is added the specific region 920, with respect to which the imaging mode has been changed, in a first region 310 according to the change information.

Figure 10A:
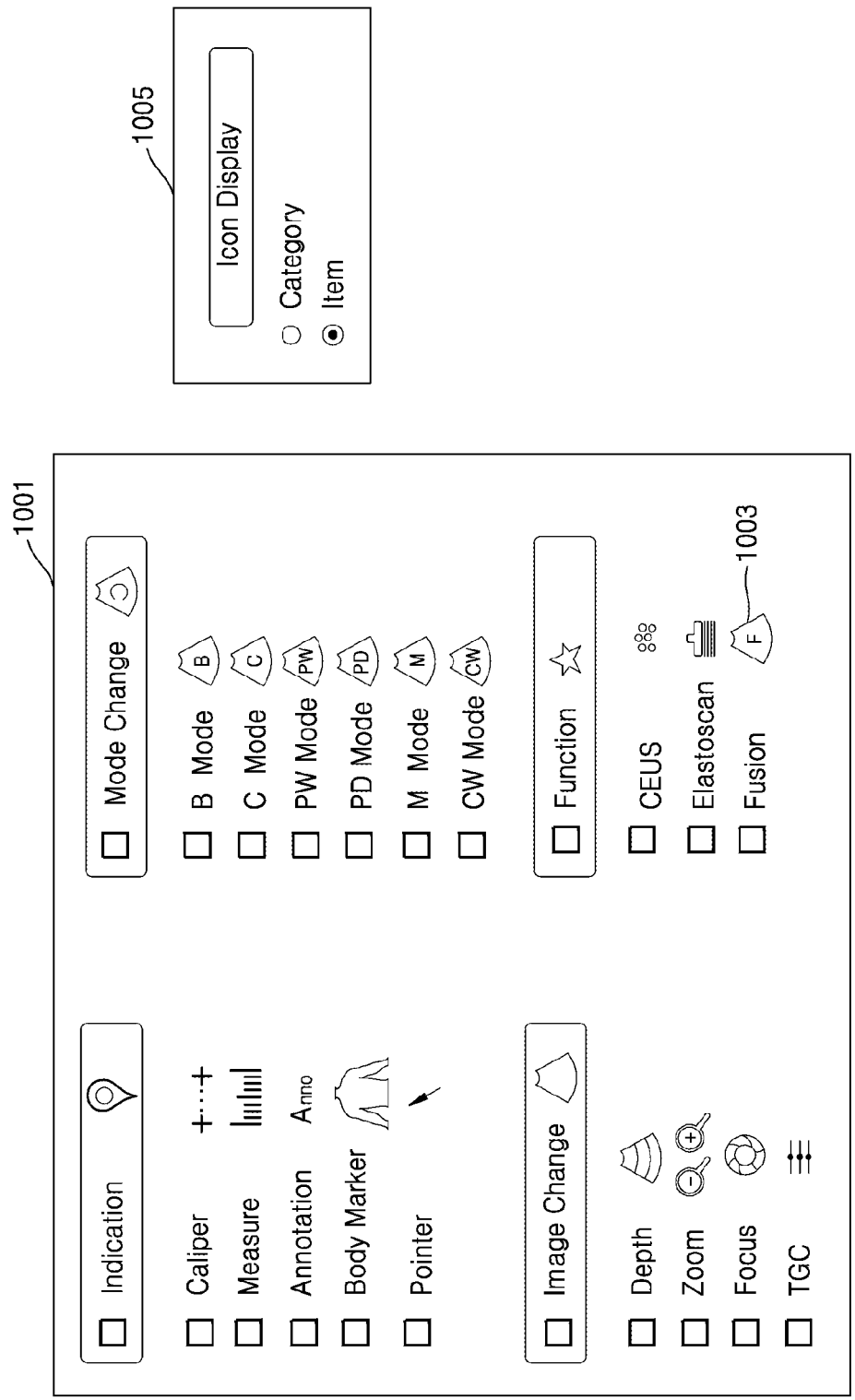
FIG. 10A is a diagram for explaining classifying and displaying of icons by an ultrasound imaging apparatus according to an exemplary embodiment.

FIG. 10A is a diagram for explaining classifying and displaying of icons by the apparatus 100 (200) according to an exemplary embodiment.

The user may preselect an icon that can be displayed in the second region 320 of FIG. 3 from among all icons generated by the apparatus 100 (200). According to an exemplary embodiment, the user may perform an input for preselecting an icon that can be displayed in the second region 320 via the user interface 120 (220). According to an exemplary embodiment, the apparatus 100 (200) may provide the user with a screen 1001 via the display 110 (210), and receive an input for selecting an icon from the user via the user interface 120 (220). According to an exemplary embodiment, the apparatus 100 (200) may provide the user with the screen 1001 and classify icons that can be selected by the user into four categories, i.e., Indication, Mode Change, Image Change, and Function categories for display thereof. Furthermore, as shown on the screen 1001, the apparatus 100 (200) may display five (5), six (6), four (4), and three (3) pieces of change information respectively included in the indication, mode change, image change, and function categories. The apparatus 100 (200) may also provide categories or pieces of change information other than the four categories and the pieces of change information included in the four categories shown on the screen 1001.

As seen on the screen 1001, according to an exemplary embodiment, the Indication category may include the 5 pieces of change information, i.e., Caliper for adding measurement information such as a length or angle of a specific portion in an ultrasound image to the ultrasound image, Measure for adding clinical information and measurement information such as a length or angle of a specific portion in an ultrasound image to the ultrasound image, Annotation for adding an annotation indicated by a letter or image to an ultrasound image, Body Marker for adding information indicating which part of a body corresponds to a specific region in an ultrasound image to the ultrasound image, and Pointer for adding an annotation having a form of a mouse pointer to an ultrasound image.

According to an exemplary embodiment, as shown on the screen 1001, the Mode Change category may include the 6 pieces of change information, i.e., Brightness (B) Mode for changing an imaging mode for an original ultrasound image to a B mode or displaying an ultrasound image in the B mode together with the original ultrasound image, Color (C) Mode for changing an imaging mode for an original ultrasound image to a C mode or displaying an ultrasound image in the C mode together with the original ultrasound image, Pulse Wave (PW) Mode for changing an imaging mode for an original ultrasound image to a PW mode or displaying an ultrasound image in the PW mode together with the original ultrasound image, Power Doppler (PD) Mode for changing an imaging mode for an original ultrasound image to a PD mode or displaying an ultrasound image in the PD mode together with the original ultrasound image, Motion (M) Mode for changing an imaging mode for an original ultrasound image to an M mode or displaying an ultrasound image in the M mode together with the original ultrasound image, and Continuous Wave (CW) Mode for changing an imaging mode for an original ultrasound image to a CW mode or displaying an ultrasound image in the CW mode together with the original ultrasound image.

According to an exemplary embodiment, as shown on the screen 1001, the Image Change category may include the 4 pieces of change information, i.e., Depth for adding depth information of an ultrasound image to the ultrasound image, Zoom for enlarging or reducing an ultrasound image, Focus for adjusting a focus of an ultrasound image, and Time Gain Compensation (TGC) for adjusting gain or image brightness according to a depth in an ultrasound image.

As shown on the screen 1001, according to an exemplary embodiment, the Function category may include the 3 pieces of change information, i.e., Contrast Enhanced Ultrasound for enhancing a contrast of an ultrasound image, Elastoscan for displaying a stiffness value of a specific portion in an original ultrasound image, and Fusion for displaying an image generated using medical imaging techniques such as CT, MRI, PET, or Digital Imaging and Communications in Medicine (DICOM) simultaneously with an original ultrasound image.

Furthermore, as seen on the screen 1001, the apparatus 100 (200) may display the categories and pieces of change information together with icons that may be selected by the user and respectively correspond to names of the categories and the pieces of change information. For example, the apparatus 100 (200) may display an icon 1003 corresponding to change information Fusion on the screen 1001.

Thus, the apparatus 100 (200) may receive an input for selecting pieces of change information that are displayed on the screen 1001 from the user, and display in the second region 320 of FIG. 3 icons corresponding to the pieces of change information selected by the user among all icons respectively corresponding to pieces of change information of a moving image. Furthermore, the apparatus 100 (200) may receive an input for selecting categories displayed on the screen 1001 and display in the second region 320 icons corresponding to the categories selected by the user among all icons corresponding to categories including pieces of change information of a moving image.

Furthermore, by providing the user with the screen 1001, the apparatus 100 (200) may receive an input for selecting a category or item from the user. In this case, an item refers to pieces of change information included in each category. In other words, the apparatus 100 (200) may receive an input for selecting a category from the user, and display icons corresponding to the category including pieces of change information of a moving image in the second region 320. The apparatus 100 (200) may also receive an input for selecting an item from the user, and display icons respectively corresponding to pieces of change information in the second region 320.

Figure 10B:
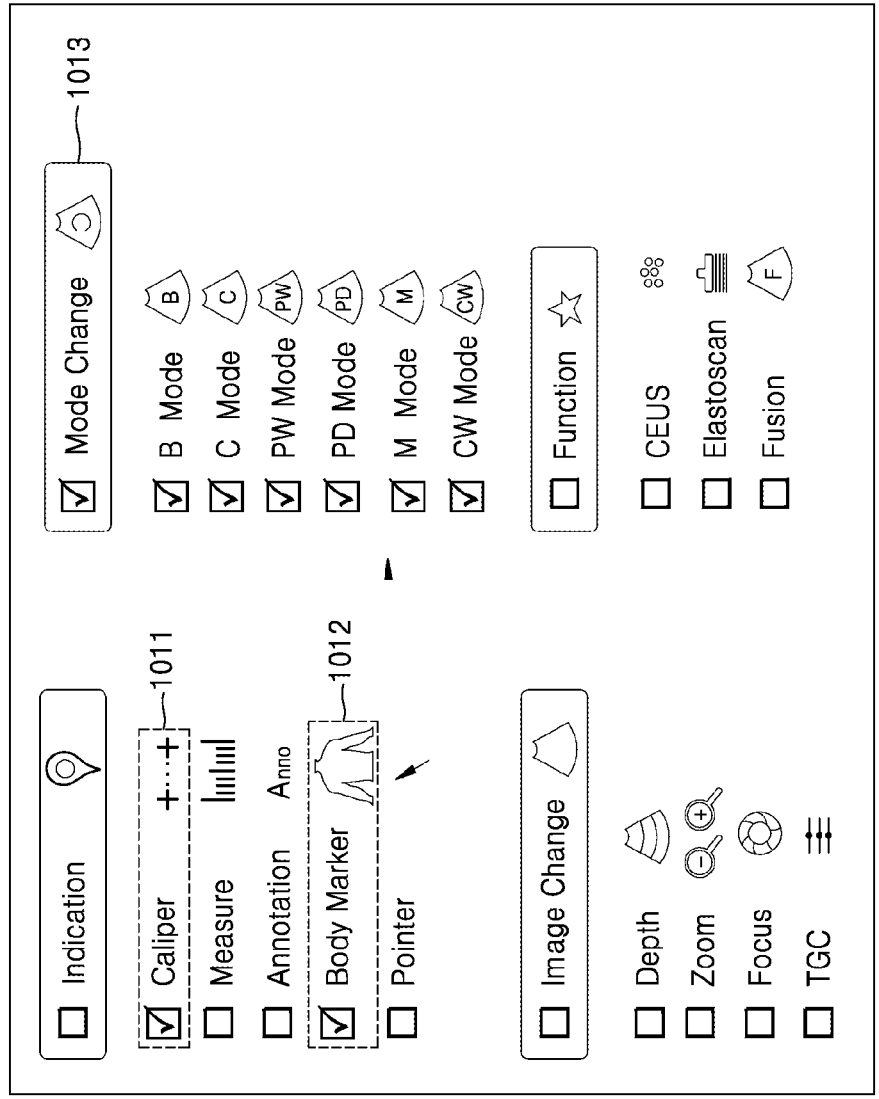
FIG. 10B is an example where an ultrasound imaging apparatus receives an input for selecting pieces of change information from the user, according to an exemplary embodiment.

FIG. 10B is an example where the apparatus 100 (200) receives an input for selecting pieces of change information from the user, according to an exemplary embodiment.

According to an exemplary embodiment, the apparatus 100 (200) may provide the user with the screen 1001 shown in FIG. 10A and receive from the user an input for selecting pieces of change information or icons respectively corresponding to the pieces of change information.

As shown in FIG. 10B, the apparatus 100 (200) may receive a user input for selecting a caliper 1011 and a body marker 1012 in Indication category. In other words, the user may select the caliper 1011 and the body marker 1012 via the user interface 120 (220) in the apparatus 100 (200).

Furthermore, the apparatus 100 (200) may receive a user input for selecting Mode Change category 1013. When the apparatus 100 (200) receives the user input for selecting the Mode Change category 1013, all pieces of change information in the Mode Change category 1013 may be selected. In other words, when the apparatus 100 (200) receives the user input for selecting the Mode Change category 1013, all the pieces of change information in the Mode Change category 1013, i.e., B Mode, C Mode, PW Mode, PD Mode, M Mode, and CW Mode, may be selected.

Figure 10C:
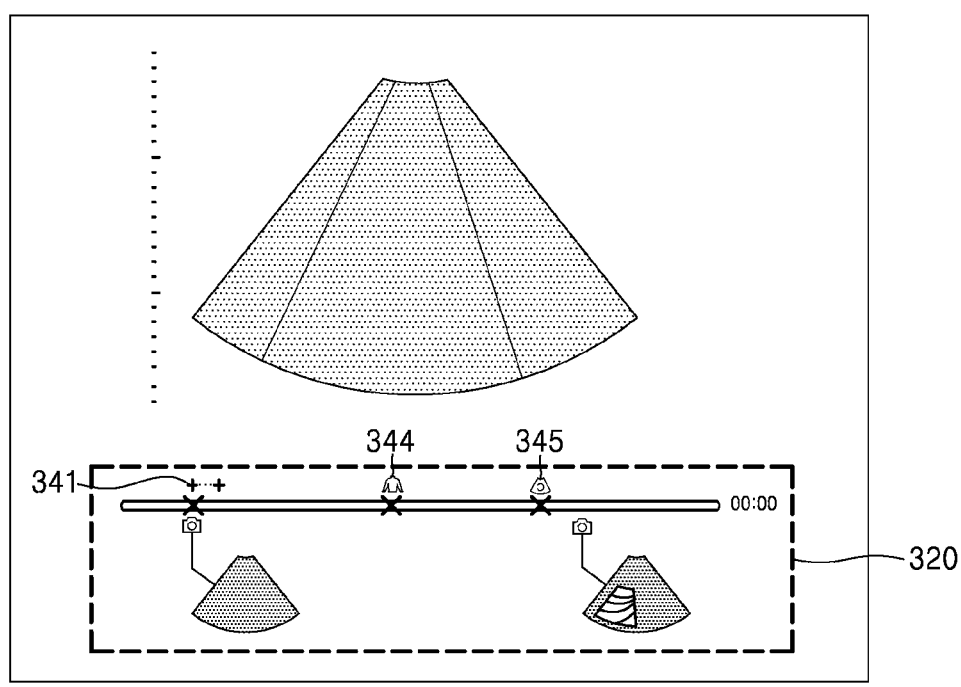
FIG. 10C is an example where an ultrasound imaging apparatus displays an ultrasound image when receiving a user input as shown in FIG. 10B, according to an exemplary embodiment.

FIG. 10C is an example where the apparatus 100 (200) displays an ultrasound image when receiving a user input as shown in FIG. 10B, according to an exemplary embodiment.

The apparatus 100 (200) may display the first and second regions 310 and 320 shown in FIG. 3 on a screen via the display 110 (210). Then, when the apparatus 100 (200) receives a user input as shown in FIG. 10B, the apparatus 100 (200) may display in the second region 320, as shown in FIG. 10C, the icons 341, 344, and 345 corresponding to pieces of change information selected via the user input from among the icons 341 through 345 shown in FIG. 3. In other words, the apparatus 100 (200) may selectively display only pieces of change information selected by the user, from among all pieces of change information that have been set in an ultrasound image.

Thus, the apparatus 100 (200) may selectively display only pieces of change information desired by the user instead of all pieces of change information that have been set in an ultrasound image.

Figure 10D:
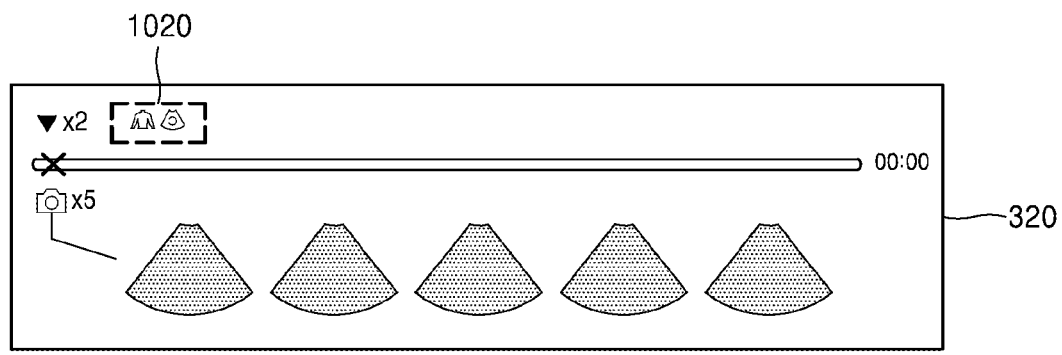
FIG. 10D is an example where an ultrasound imaging apparatus displays a second region when receiving a user input as shown in FIG. 10B, according to an exemplary embodiment.

FIG. 10D is an example where the apparatus 100 (200) displays a second region 320 when receiving a user input as shown in FIG. 10B, according to an exemplary embodiment.

The apparatus 100 (200) may display the icon 440 representing a plurality of pieces of change information as shown in FIG. 4 in the second region 320. Then, when the apparatus 100 (200) receives a user input as shown in FIG. 10B, the apparatus 100 (200) may display in the second region 320 an icon 1020 corresponding to pieces of change information selected via the user input from the icon 440 shown in FIG. 4. In other words, the apparatus 100 (200) may selectively display only pieces of change information selected by the user, from among all pieces of change information that have been set in an ultrasound image.

Thus, the apparatus 100 (200) may selectively display only pieces of change information desired by the user instead of all pieces of change information that have been set in an ultrasound image.

Figure 11:
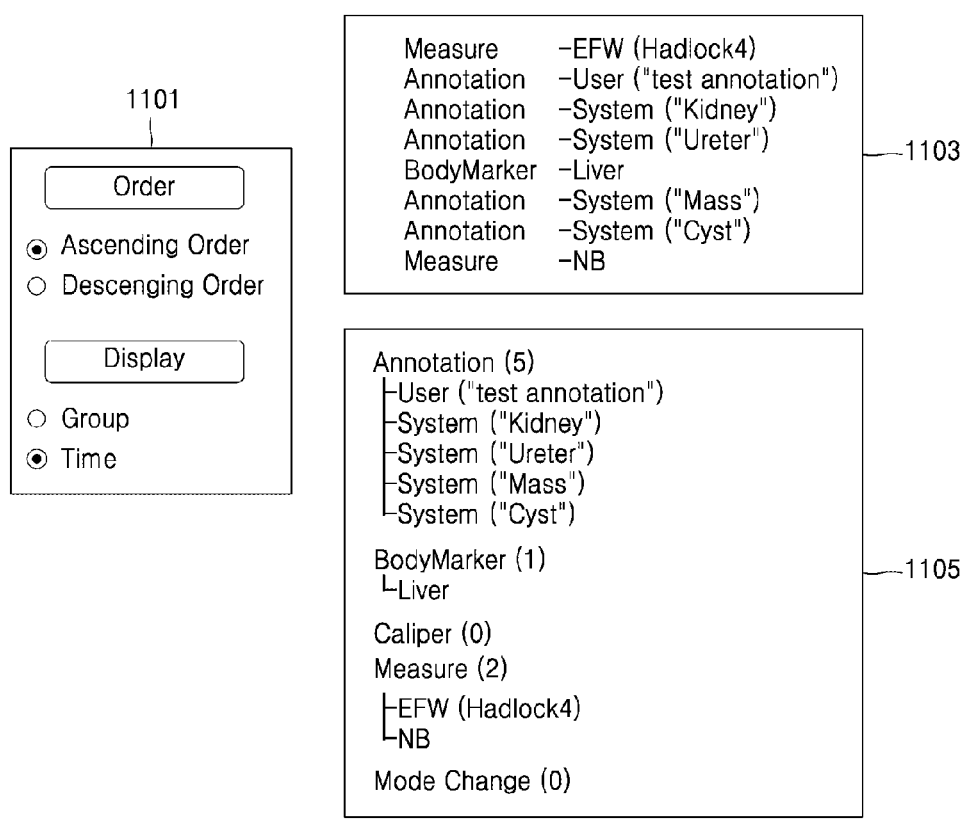
FIG. 11 is a diagram for explaining classifying and displaying of pieces of change information by an ultrasound imaging apparatus according to an exemplary embodiment.

FIG. 11 is a diagram for explaining classifying and displaying of pieces of change information by the apparatus 100 (200) according to an exemplary embodiment The apparatus 100 (200) may arrange pieces of change information of a moving image according to predetermined criteria for display thereof. According to an exemplary embodiment, the apparatus 100 (200) may provide the user with a screen 1101 to receive an input for selecting the criteria according to which the pieces of change information are arranged from the user.

According to an exemplary embodiment, if the apparatus 100 (200) receives an input for selecting Ascending Order and Group from the user, the apparatus 100 (200) may divide pieces of change information of a moving image in each category into groups and list the groups and the pieces of change information in each group in an ascending alphabetical order. For example, if the apparatus 100 (200) receives an input for selecting Ascending Order and Group from the user, the apparatus 100 (200) may provide the user with a screen 1105.

According to another exemplary embodiment, if the apparatus 100 (200) receives an input for selecting Descending Order and Group from the user, the apparatus 100 (200) may divide pieces of change information of a moving image in each category into groups and list the groups and the pieces of change information in each group in a descending alphabetical order.

According to another exemplary embodiment, if the apparatus 100 (200) receives an input for selecting Ascending Order and Time from the user, the apparatus 100 (200) may arrange piece of change information of a moving image with respect to time in an ascending order. In other words, the apparatus 100 (200) may list the pieces of change information of the moving image according to the order in which they are generated, i.e., from earliest to latest.

According to another exemplary embodiment, if the apparatus 100 (200) receives an input for selecting Descending Order and Time from the user, the apparatus 100 (200) may arrange piece of change information of a moving image with respect to time in a descending order. In other words, the apparatus 100 (200) may list the pieces of change information of the moving image according to the order in which they are generated, i.e., from latest to earliest. For example, if the apparatus 100 (200) receives an input for selecting Descending Order and Time, the apparatus 100 (200) may provide the user with a screen 1103. As shown on the screen 1105, the apparatus 100 (200) generated pieces of change information in the order of Measure (NB), Annotation ("Cyst"), and Annotation ("Mass").

Figure 12:
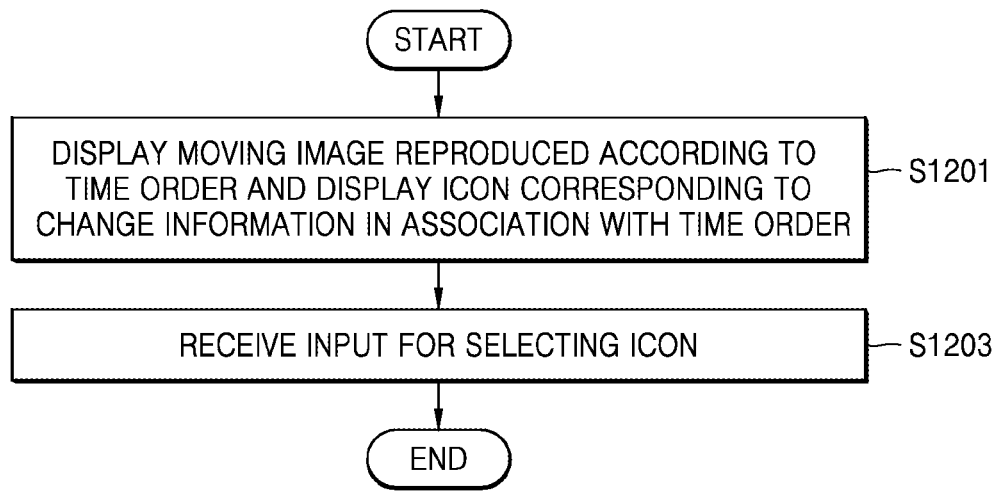
FIG. 12 is a diagram for explaining a method of processing an ultrasound image, which is performed by an ultrasound imaging apparatus, according to an exemplary embodiment.

FIG. 12 is a diagram for explaining a method of processing an ultrasound image, which is performed by the apparatus 100 (200), according to an exemplary embodiment.

Since the method of FIG. 12 may be performed by components in the apparatus 100 or 200 of FIG. 1 or 2, repeated descriptions with respect to FIGS. 1 and 2 are omitted.

Referring to FIG. 12, according to the present exemplary embodiment, the apparatus 100 (200) may display a moving image consisting of a plurality of ultrasound images that are reproduced according to a time order on a screen, together with at least one icon corresponding to at least one piece of change information for changing a display of at least one of the ultrasound images (S1201). The at least one icon may be displayed on the screen in association with the time order in which the ultrasound images are reproduced.

The apparatus 100 (200) may display a progress indicator representing the time order in which the ultrasound images of the moving image is reproduced together with icons corresponding to change information. Furthermore, the progress indicator may be displayed based on the time when a moving image is reproduced or the number of ultrasound images displayed as the moving image is reproduced.

The apparatus 100 (200) may also display a thumbnail image, corresponding to a predetermined ultrasound image among a plurality of ultrasound images, in association with the time order in which the ultrasound images of the moving image is reproduced.

Furthermore, if a plurality of pieces of change information are generated for a moving image, the apparatus 100 (200) may classify the plurality of pieces of change information according to a predetermined criterion. For example, the plurality of pieces of change information may be arranged in an ascending or descending alphabetical order or according to the order in which the pieces of change information are generated.

The apparatus 100 (200) may receive a user input for selecting an icon displayed on the screen (S1203). If the apparatus 100 (200) receives an input for selecting an icon, the apparatus 100 (200) may display an ultrasound image changed according to change information corresponding to the icon. In this case, the apparatus (100) may receive a user input for changing a display of an ultrasound image.

Furthermore, the apparatus 100 (200) may receive a user input for selecting a thumbnail image corresponding to an ultrasound image. If the apparatus 100 (200) receives an input for selecting the thumbnail image, the apparatus 100 (200) may display the ultrasound image corresponding to the thumbnail image. The apparatus 100 (200) may also receive an input for requesting a screen shot of an ultrasound image displayed on a screen.

Figure 13:
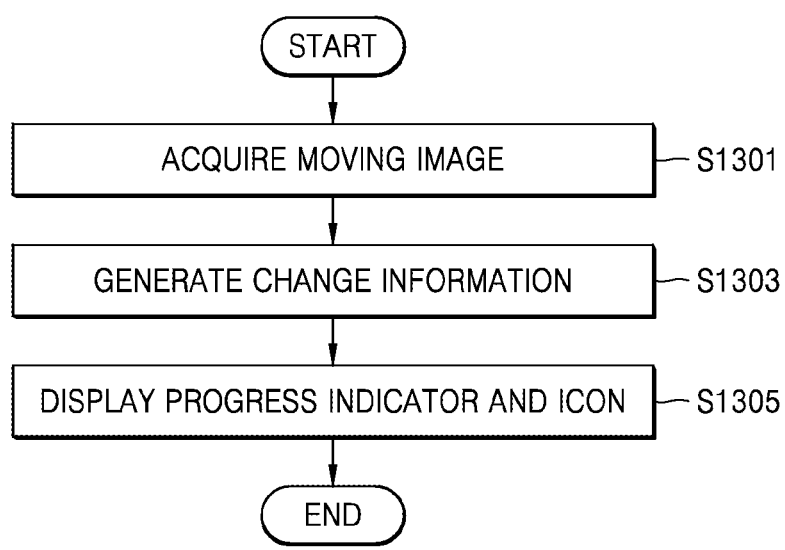
FIG. 13 is a diagram for explaining a method of processing an ultrasound image, which is performed by an ultrasound imaging apparatus, according to another exemplary embodiment.

FIG. 13 is a diagram for explaining a method of processing an ultrasound image, which is performed by the apparatus 100 (200), according to another exemplary embodiment.

Since the method of FIG. 13 may be performed by components in the apparatus 100 or 200 of FIG. 1 or 2, repeated descriptions with respect to FIGS. 1 and 2 are omitted.

The apparatus 100 (200) may acquire a moving image consisting of a plurality of ultrasound images that are sequentially reproduced (S1301). According to an exemplary embodiment, the apparatus 100 (200) may transmit an ultrasound signal to an object over a predetermined period and generate a plurality of ultrasound images of the object based on an echo signal reflected from the object. Thus, the apparatus 100 (200) may acquire a moving image from the generated ultrasound images. Furthermore, the apparatus 100 (200) may acquire a moving image in which a plurality of ultrasound images are reproduced via communication with the outside, or a prestored moving image from an internal memory.

The apparatus 100 (200) may generate change information for changing a display of an ultrasound image selected by the user from among a plurality of ultrasound images, based on a user input (S1303). The apparatus 100 (200) may also generate an icon for identifying the change information.

Furthermore, the apparatus 100 (200) may generate a thumbnail image for the selected ultrasound image based on a user input. In detail, the apparatus 100 (200) may take a screen shot of the ultrasound image to generate a thumbnail image for the ultrasound image based on a user input.

The apparatus 100 (200) may also store the generated change information or the thumbnail image as metadata.

The apparatus 100 (200) may display a progress indicator representing a progress of reproduction of the moving image and an icon identifying the change information (S1305). If the icon is selected by the user, the apparatus 100 (200) may change the selected ultrasound image according to the change information and display the changed ultrasound image.

Furthermore, the apparatus 100 (200) may display a thumbnail image together with a progress indicator. If the thumbnail image is selected by the user, the apparatus 100 (200) may display an ultrasound image corresponding to the selected thumbnail image.

In addition, the apparatus 100 (200) may classify and arrange pieces of change information according to a predetermined criterion for display thereof.

Figure 14:
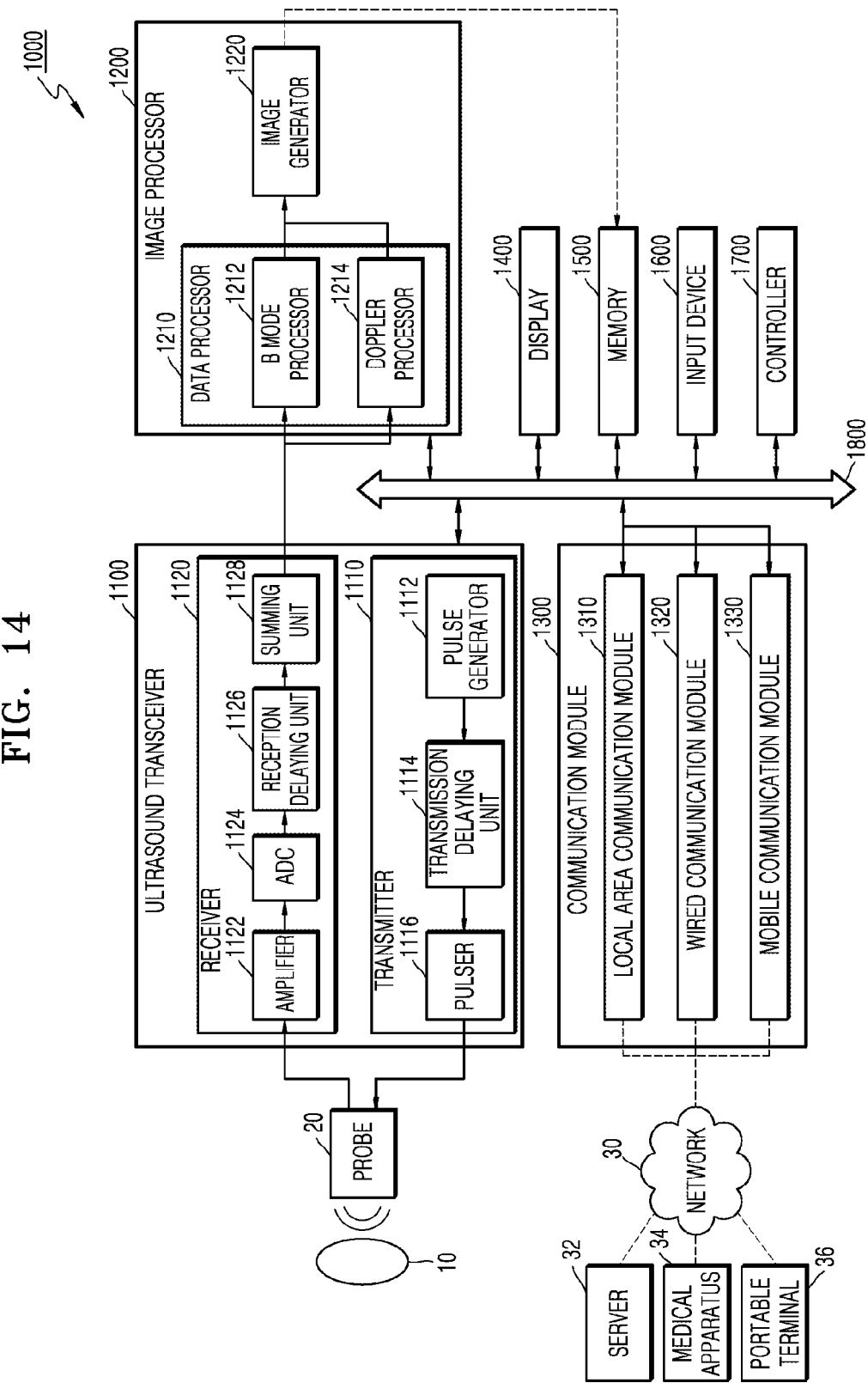
FIG. 14 is a block diagram of a configuration of an ultrasound diagnosis apparatus related to an exemplary embodiment.

FIG. 14 is a block diagram of a configuration of an ultrasound diagnosis apparatus 1000 related to an exemplary embodiment.

Methods of processing an ultrasound image according to exemplary embodiments may be performed by the ultrasound diagnosis apparatus 1000, and the apparatus 100 (200) may be included in the ultrasound diagnosis apparatus 1000.

The apparatus 100 (200) of FIG. 1 or 4 may perform some or all of the functions performed by the ultrasound diagnosis apparatus 1000. The display 110 (210) and the user interface 120 (220) may correspond respectively to a display 1400 and an input device 1600 shown in FIG. 14. The image acquisition unit 230, the controller 240, and the memory 250 shown in FIG. 2 may correspond respectively to an image processor 1200, a controller 1700, and a memory 1500 shown in FIG. 14. Furthermore, the image acquisition unit 230 may correspond to a probe 20, an ultrasound transceiver 1100, and the image processor 1200 shown in FIG. 14.

Referring to FIG. 1, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analogto-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components. According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. However, embodiments are not limited thereto, and some of the components stated above may be implemented as hardware modules. Furthermore, at least one selected from the ultrasound transceiver 1100, the image processor 1200, and the communication module 1300 may be included in the controller 1700. However, embodiments are not limited thereto.

Examples of the above-described apparatuses include a processor, a memory for storing and executing program data, a permanent storage such as a disc drive, a communication port for communicating with external devices, and a user interface device such as a touch panel, keys, or buttons. Methods implemented by using software modules or algorithms may be stored as computer-readable codes executable by the processor or program instructions on a computer-readable recording medium. Examples of the computer-readable recording medium include magnetic storage media (e.g., ROM, RAM, floppy disks, hard disks, etc.) and optical recording media (e.g., CD-ROMs and Digital Versatile Discs (DVDs)). The computer-readable recording medium may also be distributed over network-coupled computer systems so that the computer-readable codes are stored and executed in a distributed fashion. The computer-readable recording medium can be read by a computer, function as a memory, and executed by the processor.

Exemplary embodiments may be described in terms of functional block components and various processing steps. Such functional blocks may be realized by any number of hardware and/or software components configured to perform the specified functions. For example, the exemplary embodiments may employ various integrated circuit components, e.g., memory elements, processing elements, logic elements, look-up tables, and the like, which may carry out a variety of functions under the control of one or more microprocessors or other control devices. Similarly to where the elements of the exemplary embodiments are implemented using software programming or software elements, the exemplary embodiments may be implemented with any programming or scripting language such as C, C++, Java, assembler, or the like, with the various algorithms being implemented with any combination of data structures, processes, routines or other programming elements. Functional aspects may be implemented in algorithms that are executed on one or more processors. Furthermore, the exemplary embodiments may employ any number of conventional techniques for electronics configuration, signal processing and/or data processing and the like. The words "mechanism", "element", "means", and "construction" are used broadly and are not limited to mechanical or physical configurations, but may include software routines in conjunction with processors, etc.

The particular implementations shown and described herein are illustrative examples and are not intended to otherwise limit the scope of the inventive concept in any way. For the sake of brevity, conventional electronics, control systems, software development and other functional aspects of the systems may not be described in detail. Furthermore, the connecting lines or connectors shown in the various figures presented are intended to represent exemplary functional relationships and/or physical or logical couplings between the various elements. In an actual apparatus, there may be various functional, physical, or logical couplings between the elements, which may be substituted or added as appropriate.

The use of the term "the" and similar referents in the context of describing the exemplary embodiments (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the operations of all methods described herein can be performed in any suitable order unless otherwise specified herein or otherwise clearly contradicted by context. The use of any and all examples, or exemplary language (e.g., "such as") provided herein, is intended merely to better illuminate the invention and does not pose a limitation on the scope of the inventive concept unless otherwise claimed. While the present general inventive concept has been particularly shown and described with reference to exemplary embodiments thereof, it will be understood by those of ordinary skill in the art that various changes, combinations, and modifications in form and details may be made therein according to design conditions and factors without departing from the spirit and scope of the present inventive concept as defined by the following claims and their equivalents.

What is claimed is:

1. An ultrasound imaging apparatus comprising:
a probe configured to receive an echo signal;
a display; and
a processor configured to:
   generate a plurality of ultrasound images based on the echo signal, and
   control the display to display a screen including a first area in which the plurality of ultrasound images are consecutively reproduced according to a time order and a second area in which a progress bar representing a progress of reproduction of the plurality of ultrasound images over time and at least one icon, corresponding to at least one piece of change information for changing a display of at least one of the plurality of ultrasound images, in association with the time order, are displayed, and
wherein the at least one icon comprises a first icon corresponding to first change information for changing a display of a first ultrasound image of the plurality of ultrasound images and a second icon, which is different from the first icon, corresponding to second change information for changing a display of a second ultrasound image of the plurality of ultrasound images, and
wherein a type of the second change information is different from a type of the first change information.

2. The ultrasound imaging apparatus of claim 1, further comprising a user interface configured to receive a first input for selecting the first icon.

3. The ultrasound imaging apparatus of claim 2, further wherein the processor is further configured to change, if the first input is received, at least one ultrasound image according to the at least one piece of change information and control the changed at least one ultrasound image to be displayed via the display.

4. The ultrasound imaging apparatus of claim 2, wherein the processor is further configured to control the display to display at least one thumbnail image corresponding to the at least one ultrasound image from among the plurality of ultrasound images according to the time order,
wherein the user interface is configured to receive a second input for selecting the at least one thumbnail image, and the processor is further configured to control, if the second input is received, the at least one ultrasound image corresponding to the at least one thumbnail image to be displayed via the display.

5. The ultrasound imaging apparatus of claim 1, wherein the at least one piece of change information comprises at least one selected from the group consisting of information for inserting a predetermined letter or image into the at least one ultrasound image, information for changing an imaging mode for the at least one ultrasound image, and information for enlarging or reducing the at least one ultrasound image.

6. The ultrasound imaging apparatus of claim 1, wherein the processor is further configured to control the display to display the first icon at a position adjacent to a time point within the progress bar when the first ultrasound image is displayed.

7. The ultrasound imaging apparatus of claim 1, wherein the progress bar is displayed based on a time when the plurality of ultrasound images are displayed or based on a number of ultrasound images displayed among the plurality of ultrasound images.

8. The ultrasound imaging apparatus of claim 1, wherein the processor is further configured to control the display to display the first change information and the second change information that are classified according to a predetermined criterion or arranged according to an order in which the first change information and the second change information are generated.

9. The ultrasound imaging apparatus of claim 1, further comprising:
   an image acquisition unit configured to acquire the plurality of ultrasound images; and
   a memory configured to store the at least one piece of change information as metadata,
   wherein the processor is configured to generate the at least one piece of change information based on a user input.

10. The ultrasound imaging apparatus of claim 9, wherein the image acquisition unit transmits an ultrasound signal to an object over a predetermined period.

11. The ultrasound imaging apparatus of claim 1, further comprising:
   a user interface configured to receive a first input for stopping a consecutive display of the plurality of ultrasound images based on a first ultrasound image,
   wherein the processor is configured to generate the first change information for changing a display of the first ultrasound image based on a second input received via the user interface, and
   wherein the display displays the first icon corresponding to the first change information in association with the time order.

* * * * *